(12) United States Patent
Omori et al.

(10) Patent No.: US 8,029,878 B2
(45) Date of Patent: Oct. 4, 2011

(54) MEDICAL CONTAINER AND MEDICAL DUPLEX CONTAINER

(75) Inventors: Kenji Omori, Zushi (JP); Takeshi Nizuka, Otsu (JP); Dai Sudo, Shizuoka (JP); Manabu Fujimoto, Osaka (JP); Masashi Moteki, Anpachi-Gun (JP); Toyoaki Suzuki, Tokyo (JP); Koichi Miura, Tokyo (JP); Kaori Ikeda, Hyogo (JP); Hideji Kashiwagi, Hyogo (JP); Hidetoshi Myojyo, Hyogo (JP)

(73) Assignees: Nipro Corporation, Osaka (JP); Fujimori Kogyo Co., Ltd., Tokyo (JP); Shionogi & Co., Ltd., Osaka (JP)

( * ) Notice: Subject to any disclaimer, the term of this patent is extended or adjusted under 35 U.S.C. 154(b) by 0 days.

(21) Appl. No.: 11/663,886

(22) PCT Filed: Sep. 26, 2005

(86) PCT No.: PCT/JP2005/017634
§ 371 (c)(1),
(2), (4) Date: Mar. 27, 2007

(87) PCT Pub. No.: WO2006/035718
PCT Pub. Date: Apr. 6, 2006

(65) Prior Publication Data
US 2008/0044606 A1    Feb. 21, 2008

(30) Foreign Application Priority Data

Sep. 27, 2004 (JP) ................ P2004-280124
Sep. 29, 2004 (JP) ................ P2004-284814

(51) Int. Cl.
*B32B 1/02* (2006.01)
*B32B 1/08* (2006.01)

(52) U.S. Cl. ............. 428/35.7; 428/34.1; 428/34.2; 428/35.9; 428/36.9

(58) Field of Classification Search ........... 428/34.1, 428/34.2, 35.9, 36.9, 35.7
See application file for complete search history.

(56) References Cited

U.S. PATENT DOCUMENTS
5,468,803 A    11/1995    Takahashi et al.
(Continued)

FOREIGN PATENT DOCUMENTS
CA    2369137 A1    10/2000
(Continued)

OTHER PUBLICATIONS

May 17, 2010 State Intellectual Property Office, P.R. China, Office Action for Application No. JP200580032586.9, partial translation.
(Continued)

*Primary Examiner* — Marc A Patterson
(74) *Attorney, Agent, or Firm* — Birch, Stewart, Kolasch & Birch, LLP (57) ABSTRACT

A medical container comprising a body for containing a medicament, the body of the medical container being formed of a multilayered film comprising (i) a layer formed of a linear polyolefin and (ii) a layer formed of a cyclic polyolefin adjacent to the layer (i), and the layer (i) formed of the linear polyolefin satisfying the following conditions (a) and/or (b):
Condition (a): an amount of a liquid component, which remains after Soxhlet's extraction with organic solvents followed by evaporation of the solvents, is 0.2% by weight or less, and
Condition (b): a branching degree of a component, which remains after Soxhlet's extraction with n-hexane followed by evaporation of n-hexane, is 50 or less per 1,000 carbon atoms.

18 Claims, 2 Drawing Sheets

U.S. PATENT DOCUMENTS

| | | |
|---|---|---|
| 5,561,208 A | 10/1996 | Takahashi et al. |
| 5,706,937 A | 1/1998 | Futagawa et al. |
| 5,811,047 A | 9/1998 | Inoue et al. |
| 6,140,439 A * | 10/2000 | Brookhart et al. ............ 526/308 |
| 2006/0165928 A1 | 7/2006 | Suzuki et al. |

FOREIGN PATENT DOCUMENTS

| | | |
|---|---|---|
| DE | 19916141 A1 | 10/2000 |
| EP | 0737468 | 10/1996 |
| JP | 4-276253 A | 10/1992 |
| JP | 5-317411 A | 12/1993 |
| JP | 8-155007 A | 6/1996 |
| JP | 8-280775 A | 10/1996 |
| JP | 2826643 B2 | 9/1998 |
| JP | 2001-162724 A | 6/2001 |
| JP | 2003192053 A | 7/2003 |
| JP | 2004167800 A | 6/2004 |
| JP | 2004121824 A | 11/2005 |
| WO | WO-94/06396 A1 | 3/1994 |
| WO | WO-2004/080370 A1 | 9/2004 |

OTHER PUBLICATIONS

European Search Report, issued by the European Patent Office on Jun. 1, 2011.

* cited by examiner

MEDICAL CONTAINER AND MEDICAL DUPLEX CONTAINER

This application is the U.S. National Stage under 35 USC §371 of International Application PCT/JP2005/017634 filed on Sep. 26, 2005, which claims priority under 35 USC §119 (a)-(d) of Japanese Application No. 2004-280124 filed on Sep. 27, 2004, and Japanses Application No. 2004-284814 filed on Sep. 29, 2004.

TECHNICAL FIELD

The present invention relates to a container comprising one or plural (for example, two) compartments formed of a material comprising plural layers, for example, a medical container (for convenience, such a container can also be referred to as a "medical multilayered container") and, more particularly, to a container which suppresses elution of a component from the material constituting the container, for example, a medical container. For convenience, a medical container comprising the plural compartments is referred to as a "medical duplex container" or a "medical multilayered duplex container".

BACKGROUND ART

Heretofore, as a container containing a medicament, there has widely been used a container using a single-layered film formed of a linear polyolefin or a multilayered film comprising a linear polyolefin layer and a polymer layer having barrier properties against moisture or a gas. Also, the use of a multilayered film comprising these films bonded to each other using an adhesive has recently been approved by revision of the Pharmacopoeia in Japan and a medical container provided with various performances has been developed, and thus it becomes possible to contain various medicaments in such a container.

However, since it has become possible to contain various medicaments as a result of the improvement in the performances of the container, there may arise problems such as decrease in the content of an active ingredient of a medicament due to an interaction between a low molecular weight component eluted into the container from the linear polyolefin layer and/or the adhesive layer, increase in the content of related substances, increase in the content of insoluble fine particles in a liquid medicament and the like.

Under these circumstances, there is an apprehension that any adverse influence is exerted on the medicament to be packed. To dispel such an apprehension, there has been proposed, as a polyolefin packing material which is less likely to be adversely influence, a polyolefin packing material for packing a medicament, which contains 150 ppm or less of a substance having 12 or more and 26 or less carbon atoms, and is obtained by treating a linear low-density polyethylene resin at a resin temperature of 170 to 230° C. under reduced pressure of 10 Torr or less using a Vent-type extruder (see Japanese Patent No. 2,826,643 which is referred to below). Also, as a packing material for foods, beverages or drugs, which is less likely to cause elution of a low molecular weight substance, there hwe been proposed a low elution packing material obtained by laminating a sealant layer (for example, a linear low-density polyethylene or non-stretched polypropylene film) on a base material via a cyclic olefin copolymer layer or a blend polymer layer formed of a cyclic olefin copolymer and a polyolefin resin (see Japanese Unexamined Patent Publication (Kokai) No. 2001-162724 which is referred to below)[0005]

However, a medical container using these packing materials has a problem in that when a drug is a solid medicament (for example, a powdered medicament) which is mixed with a dissolving liquid to prepare a liquid medicament upon use, insoluble fine particles in the liquid medicament increase. Also, it is required for such a medical container to have suitability as to radiation exposure upon irradiation sterilization, in addition to the suitability as to high temperature sterilization such as high pressure steam sterilization, hot water sterilization or the like.

Patent Reference 1: Japanese Patent No. 2,826,643
Patent Reference 1: Japanese Unexamined Patent Publication (Kokai) No. 2001-162724

DISCLOSURE OF THE INVENTION

Problems of the Invention

A problem of the present invention is to provide a container, for example, a medical container which can be subjected to the irradiation sterilization and which decreases an amount of a component eluted into the inside of the medical container from a material constituting the medical container (for example, the component being a low molecular weight component eluted from a layer constituting the material, an adhesive layer component used to bond such layer, etc.), thereby alleviating problems of an adverse influence due to an interaction between these components and a medicament in the medical container (for example, the adverse influence being decrease in the content of the medicament, increase in the content of related substances of the medicament, increase in the content of insoluble fine particles in the medicament and the like), preferably solving the problems, and also has medicament stability. Particularly, the present invention provides a duplex container, for example, a medical duplex container in which, after radiation sterilization, a solid medicament container aseptically filled with a solid medicament such as a powdered medicament is bonded with a liquid agent container subjected to high pressure steam sterilization after being filled with a liquid agent. When such duplex container is used so as to formulate an objective medicament by mixing the solid medicament with the liquid agent, at least one of the following problems is suppressed and preferably is substantially overcome: deterioration of a stored solid medicament; increase in the content of the insoluble fine particles in the formulated medicament; change in appearance of the solid medicament container caused by the irradiation sterilization and the like in a comparison with a conventionally used medical duplex container when the objective medicament is formulated by mixing the solid medicament stored for a long period with the liquid agent.

Means to Solve the Problems

The present inventors have intensively studied so as to solve the above problems and found that the above objects are achieved when as a material constituting a container such as a medical container, a multilayered film is used which comprises a linear polyolefin layer as an innermost layer and a cyclic polyolefin layer adjacent to the linear polyolefin layer, and furthermore when upon paying attention to the linear polyolefin, the linear polyolefin contains a specific amount of a specific liquid component (condition (a)) as described hereinafter, or the linear polyolefin contains a specific component having a specific branching degree (condition (b)) as described hereinafter, and thus the present invention has been completed.

The condition (a) and condition (b) are as follows:

Condition (a): a total amount of liquid components, which remains after Soxhlet's extraction of the linear polyolefin layer with using predetermined organic solvents (four solvents: methanol, acetone, n-pentane and n-hexane) in the above described sequence followed by evaporation of the solvents respectively, is 0.2% by weight or less; and Condition (b): a branching degree of a component, which remains after Soxhlet's extraction of the linear polyolefin layer with n-hexane followed by evaporation of n-hexane, is 50 or less per 1,000 carbon atoms.

Furthermore, it has been found that it is more preferable to satisfy both conditions (a) and (b). Therefore, the present invention provides three kinds of containers, for example, medical containers, that is, a container formed using a multilayered film comprising a linear polyolefin layer which satisfies the condition (a), a container formed using a multilayered film comprising a linear polyolefin layer which satisfies the condition (b), and a container formed using a multilayered film comprising a linear polyolefin layer which satisfies the conditions (a) and (b).

In addition, it has been found that it is more preferable that the multilayered film further comprises a layer formed of a linear polyolefin adjacent to the cyclic polyolefin layer, if necessary.

In the present description, the term "adjacent" means the state in being directly contacted. Therefore, the state where two layers are adjacent to each other means a state where no other material (for example, a layer formed of an adhesive) is present between one layer and the other layer). The term "lamination (or laminate)" means that two or more layers are superimposed, or means a state where two or more layers are being superimposed. In this case, the other material (for example, a layer formed of an adhesive resin or an adhesive, that is, an adhesive layer) may be present or may be absent between the layer and the layer located next to such layer.

Therefore, the present invention provides, in one embodiment, a medical container comprising a body for containing a medicament, the body being formed of the multilayered film comprising (i) the layer formed of the linear polyolefin and (ii) the layer formed of the cyclic polyolefin adjacent to said layer (i), the layer (i) formed of the linear polyolefin satisfying that (a) the amount of the liquid component, which remains after Soxhlet's extraction with the organic solvents followed by the evaporation of the solvents, is 0.2% by weight or less.

The present invention provides, in another embodiment, a medical container comprising a body for containing a medicament, the body being formed of the multilayered film comprising (i) the layer formed of the linear polyolefin and (ii) the layer formed of the cyclic polyolefin adjacent to the layer (i), the layer (i) formed of the linear polyolefin satisfying that (b) the branching degree of the component, which remains after Soxhlet's extraction with n-hexane followed by the evaporation of n-hexane, is 50 or less per 1,000 carbon atoms.

The present invention provides, in a further embodiment, a medical container comprising a body for containing a medicament, the body of the medical container being formed of the multilayered film comprising (i) the layer formed of the linear polyolefin and (ii) the layer (i) formed of the cyclic polyolefin adjacent to the layer (i), the layer (i) formed of the linear polyolefin satisfying that (a) the amount of the liquid component, which remains after Soxhlet's extraction with the organic solvents followed by the evaporation of the solvents, is 0.2% by weight or less, and (b) the branching degree of the component, which remains after Soxhlet's extraction with n-hexane followed by the evaporation of n-hexane, is 50 or less per 1,000 carbon atoms.

With respect to the above mentioned medical container of the present invention, in a preferable aspect, the body comprises a port capable of communicating the inside of the container with the outside of the container. This port can be used to supply a medicament into the container or to take out the medicament from the inside of the container.

With respect to the above mentioned medical container of the present invention, in a preferable aspect, the body constitutes a liquid agent compartment containing a liquid agent and a medicament compartment liquid-tightly connected with the liquid agent compartment via a peelable seal portion, the body being a bag-shaped container composed of a front sheet and a rear sheet, at least one of the liquid agent compartment and the medicament compartment comprising a port, and the front sheet being formed of the above mentioned multilayered film. Such a medical container is referred to as a so-called medical duplex container.

Effects of the Invention

According to the container of the present invention such as a medical container, by using the multilayered film comprising the layer formed of the specific linear polyolefin, the layer formed of the cyclic polyolefin adjacent to the layer, and if necessary, the layer formed of the linear polyolefin (the layer located on the layer formed of the cyclic layer) as a base material of the container so that the layer formed of the linear polyolefin locates as an innermost layer, it becomes possible to provide a container such as a medical container, which decreases the amount of a low molecular weight component as well as adhesive component eluted from the container, and also which alleviates or solves the problems such as increase in the amount of the insoluble fine particles in the medicament. Also, the present invention provides an effect which allows the irradiation sterilization in place of the steam sterilization.

Furthermore, with the medical duplex container, when a solid medicament as the medicament stored for a long period is formulated into an objective medicament using a liquid medicament, it becomes possible to further decrease the number of the insoluble fine particles in the formulated medicament. In addition, in the present invention, by using the layer formed of the specific linear polyolefin as the innermost layer, plural compartments, for example, the medicament compartment and the liquid compartment can be weakly fused to form a peelable seal portion between these compartments (that is, weekly bonded seal portion, therefore, a weak seal portion (easily-peelable portion)) and thus it becomes possible that the seal portion is peeled (or broken) when used, so that the materials contained in the respective compartments, for example, a medicament and a liquid medicament, are mixed and thus the objective medicament can be formulated and discharged.

BRIEF DESCRIPTION OF THE DRAWINGS

In FIG. 3 to FIG. 6, an adhesive layer, which is optionally formed between layers, is omitted.

DESCRIPTION OF REFERENCE NUMERALS

1: Medical duplex container
2: Liquid agent compartment
3: Medicament compartment
4: Front sheet
5: Rear sheet
6: Seal portion
7: Port

MODES FOR CARRYING OUT THE INVENTION

In the present invention, the medical container means a container used in the case of general medical or diagnosis practices which container comprises a body for containing a medicament (preferably with a port attached to the body), which body is formed of the multilayered film comprising plural layers. The medical or diagnosis practices include, for example, a practice such as medication through intravenous drip of a medicament such as an antibiotic agent. The container, particularly, the medical container of the present invention may have various forms, for example, a bag-shaped container, a bottle, a tube, a cell and a prefilled syringe, and includes a container containing one or more medicaments. In the present invention, the multilayered film which comprises at least the innermost layer, among the above plural layers, formed of the specific linear polyolefin, and the layer formed of the cyclic polyolefin adjacent to that layer is used to from the container, for example, the medical container.

In the present invention, the medical duplex container is a container in which a compartment containing a liquid agent and a compartment containing a medicament are partitioned in a liquid-tight state by a peelable seal portion, and the seal portion is peeled when used, thereby mixing the liquid agent with the medicament, and thus a formulated medicament is prepared. The number of the compartment containing the liquid agent and that of the compartment containing the medicament may be one or more, and two kinds of compartments are properly defined via the seal portion according to the objective formulated medicament. In the medical duplex container, at least one of the compartment containing the liquid agent and the compartment containing the medicament may have various forms such as a bag-shaped container, a bottle and a prefilled syringe similarly to the above described medical container, and such compartment is formed by using, as a base material, the multilayered film comprising at least one layer of the specific linear polyolefin layer and the cyclic polyolefin layer adjacent to the linear polyolefin layer, similarly to the above described medical container. In a preferable embodiment, at least one of the compartment containing the liquid agent is formed using such a multilayered film.

At least one of the compartments of the multilayered duplex container may be provided with a port, which functions as a medicament discharging-out portion and/or a medicament introducing portion. In the medical container or medical duplex container, it is not necessarily that the compartment or at least one compartment is entirely composed of the above described multilayered film, and at least a portion of the compartment may be composed of the above described multilayered film. As a matter of course, it is preferable that at least one of faces constituting the compartment is composed of the above described multilayered film, and it is more preferable that all of such faces are composed of the above described multilayered film.

In one embodiment of the medical container according to the present invention, the multilayered film further comprises a printable layer and/or a barrier layer on an at least two-layered film comprising (i) the layer formed of the linear polyolefin and (ii) the layer formed of the cyclic polyolefin adjacent to the layer (i). In this case, the layer (i) formed of the linear polyolefin satisfies that (a) the amount of the liquid component, which remains after the Soxhlet's extraction with the organic solvents followed by the evaporation of the solvents, is 0.2% by weight or less, and/or that (b) the branching degree of the component, which remains after the Soxhlet's extraction with n-hexane followed by the evaporation of n-hexane, is 50 or less per 1,000 carbon atoms.

In another embodiment of the medical container according to the present invention, the multilayered film further comprises a printable layer and/or a barrier layer on an at least three-layered film comprising (i) the layer formed of the linear polyolefin, (ii) the layer formed of the cyclic polyolefin adjacent to the layer (i) and (v) a layer formed of a linear polyolefin adjacent to the layer (ii). In this case, the layer (i) formed of the linear polyolefin satisfies that (a) an amount of the liquid component, which remains after the Soxhlet's extraction with the organic solvents followed by the evaporation of the solvents, is 0.2% by weight or less, and/or that (b) the branching degree of the component, which remains after the Soxhlet's extraction with n-hexane followed by the evaporation of n-hexane, is 50 or less per 1,000 carbon atoms.

In the present invention, the printable layer means a layer which can be printed with a medium such as printing ink for displaying characters, patterns or the like on the container. Also, the barrier layer is a layer having a performance capable of blocking the passage of moisture and/or a gas, for example, a gas barrier layer. In the present invention, the printable layer includes, for example, a polyester resin layer formed of polyethylene terephthalate, polyamide or polypropylene, and the polyester resin layer may comprise a polyester resin layer having an inorganic substance deposited tin film obtained by vapor deposition of an inorganic substance such as silica, aluminum, alumina or the like. These resin films are preferably monoaxially or biaxially stretched. Also, specific examples of the barrier layer include a metal foil, a metal deposited layer, an inorganic substance deposited layer and a synthetic resin layer, and the metal foil includes, for example, an aluminum foil. Examples of the metal inorganic substance deposited layer include an aluminum deposited layer and an alumina deposited layer. Examples of the inorganic substance deposited layer include an oxide deposited layers such as a silica deposited layer and an alumina deposited layer. Examples of the synthetic resin layer include layers formed of an ethylene-vinyl alcohol copolymer and a polyvinylidene chloride.

In more specific embodiment of the present invention, the multilayered film comprises (i) the layer formed of the linear polyolefin as an innermost layer and (ii) the layer formed of the cyclic polyolefin adjacent to the layer (i), and further comprises (iii) a polyester layer or a polyester layer having an inorganic substance deposited thin film and (v) the linear polyolefin layer, these layers being laminated in the above described sequence.

Furthermore, in a further specific embodiment of the medical container of the present invention, the multilayered film comprises (i) the layer formed of the linear polyolefin as an innermost layer, (ii) the layer formed of the cyclic polyolefin adjacent to the layer (i), (iv) a metal foil, a metal deposited layer or an inorganic substance deposited layer and (iii) the polyester layer or the polyester layer having the inorganic substance deposited thin film, these layers being laminated in the above described sequence.

Figure 3:
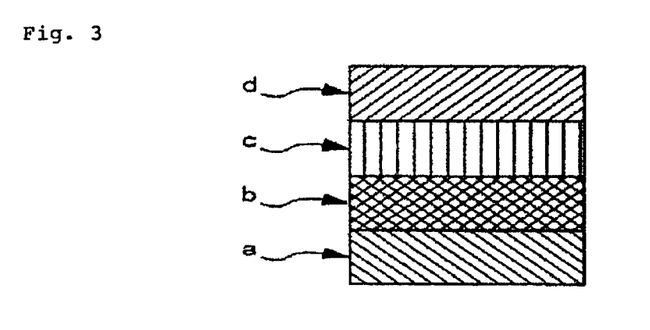
FIG. 3 is a sectional view schematically showing a multi-layered film (front sheet) which constitutes a medical container of the present invention.
Figure 4:
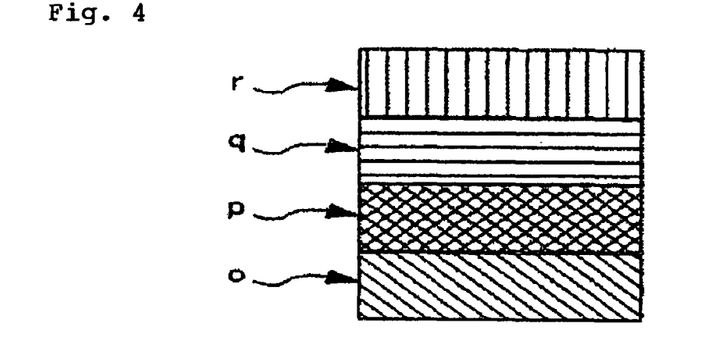
FIG. 4 is a sectional view schematically showing a multilayered film (rear sheet) which constitutes a medical container of the present invention.

Specific examples of such multilayered film which constitutes the medical container of the present invention are schematically shown in FIG. 3 and FIG. 4, respectively. In FIG. 3, the symbol "a" denotes a layer (i) formed of the above specific linear polyolefin (the innermost layer), the symbol "b" denotes a layer (ii) formed of a cyclic polyolefin (an intermediate layer), the symbol "c" denotes a polyester layer or a polyester layer (iii) having an inorganic substance deposited thin film (an intermediate layer), and the symbol "d" denotes a linear polyolefin layer (v) (the outermost layer). The layer (v) may be a layer formed of the same linear polyolefin as in the layer (i), or may be a layer formed of a different olefin (which may or may not satisfy the condition (a) and/or the condition (b)). In FIG. 4, the symbol "o" denotes a layer (i) formed of the linear polyolefin (the innermost layer), the symbol "p" denotes a layer (ii) formed of the cyclic polyolefin (an intermediate layer), the symbol "q" denotes a metal foil, a metal deposited layer or an inorganic substance deposited layer (iv) (an intermediate layer), and the symbol "r" denotes a polyolefin layer (iii) (the outermost layer).

In a still further more specific embodiment of the medical container of the present invention, the multilayered film comprises at least five layers, for example, (i) a layer formed of the linear polyolefin as the innermost layer, (ii) a layer formed of the cyclic polyolefin adjacent to the layer (i) and (v) a layer formed of the linear polyolefin adjacent to the layer (ii), and further (iii) a polyester layer or a polyester layer having an inorganic substance deposited thin film and (v) a linear polyolefin layer, these layers being laminated in the above described sequence.

Figure 5:
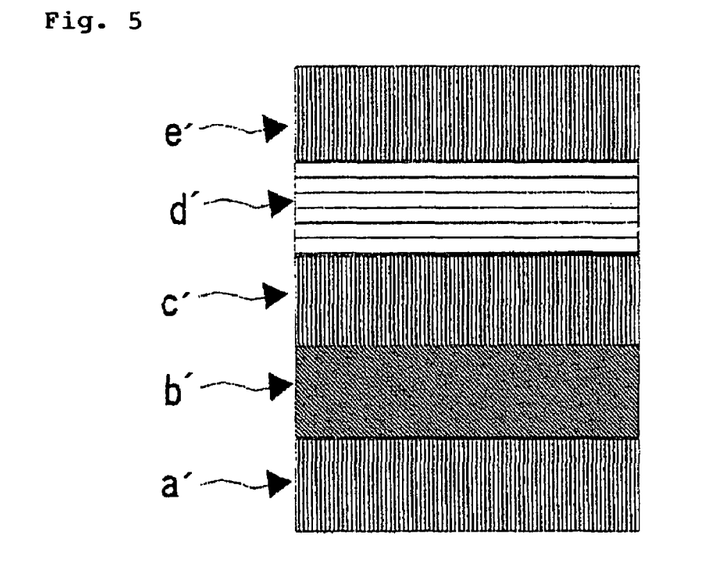
FIG. 5 is a sectional view schematically showing a multilayered film (front sheet) which constitutes a medical container of the present invention.
Figure 6:
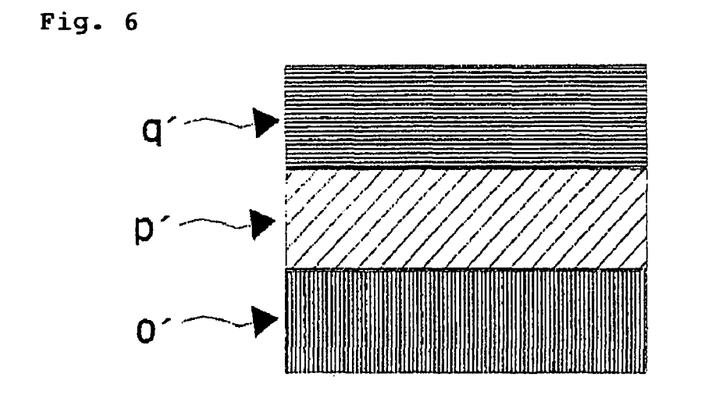
FIG. 6 is a sectional view schematically showing a multilayered film (rear sheet) which constitutes a medical container of the present invention.

Specific examples of the multilayered film as described above that constitutes the medical container of the present invention are schematically shown in sectional views of FIG. 5 and FIG. 6, respectively. In FIG. 5, the symbol "a'" denotes a layer (i) formed of the linear polyolefin (the innermost layer), the symbol "b'" denotes a layer (ii) formed of the cyclic polyolefin (an intermediate layer), the symbol "c'" denotes a linear polyolefin layer (v) (an intermediate layer), the symbol "d'" denotes a polyester layer or a polyester layer having an inorganic substance deposited thin film (iii) (an intermediate layer), and the symbol "e'" denotes a linear polyolefin layer (v) (the outermost layer). In FIG. 6, the symbol "o'" denotes a layer (i) formed of the linear polyolefin (the innermost layer), the symbol "p'" denotes a metal foil, a metal deposited layer or an inorganic substance deposited layer (iv) (an intermediate layer), and the symbol "q'" denotes a polyester layer (iii) (the outermost layer).

In a schematic sectional views of the multilayered films used in the medical container of the present invention, an adhesive layer for bonding a layer with other layer, which is optionally present, is not shown.

In the present invention, examples of the linear polyolefin include a homopolymer of an olefin such as ethylene or propylene, a copolymer of ethylene and an α-olefin and so on. Examples of the α-olefin, which is copolymerizable with ethylene, include propylene, buten-1, hexane-1, 4-methylpentene-1, octene-1 and so on. The linear polyolefin can also be said to be a polyolefin which is not a cyclic polyolefin.

Examples of the polyethylene (including a homopolymer or a copolymer) include a high-density polyethylene=HDPE (0.946 g/cm$^3$ to 0.965 g/cm$^3$), a middle-density polyethylene=MDPE (0.926 g/cm$^3$ to 0.945 g/cm$^3$), a low-density polyethylene=LDPE (0.910 g/cm$^3$ to 0.925 g/cm$^3$) and an ultralow-density polyethylene=ULDPE (0.885 g/cm$^3$ to 0.909 g/cm$^3$) on the basis of the density. Also, the polyethylene may be an LLDPE: linear low-density polyethylene prepared by copolymerizing ethylene with olefin.

Among the above described linear polyolefins, the polyethylene is preferably used in the present invention, and the density of the polyethylene is preferably from 0.932 g/cm$^3$ to 0.965 g/cm$^3$. Particularly, the middle-density polyethylene is preferably used.

As described above, in the present invention, regarding the layer (i) formed of the linear polyolefin, an amount of the liquid component, which remains after the Soxhlet's extraction with the organic solvents followed by the evaporation of the solvents, is 0.2% by weight or less (condition (a)). This means that the total of an amount of a liquid component, which remains after the Soxhlet's extraction of the linear polyolefin with a polar organic solvent (concretely, methanol) followed by the evaporation of the organic solvent from the resulting extract solution and amounts of liquid components, each of which remains after the Soxhlet's extractions of the insoluble residue of the previous Soxhlet's extraction with a nonpolar organic solvent followed by the evaporation of the nonpolar solvent from the resulting extract solution while using four nonpolar organic solvents in sequence, is 0.2% by weight or less based on the weight of the initial linear polyolefin.

After the Soxhlet's extractions with n-pentane and n-hexane in sequence, the solvents are evaporated by heating extract solutions and the remaining liquid components are weighed.

It is necessary that the total weight of the liquid components is 0.2% by weight or less. When the weight was more than 0.2% by weight, and a liquid medicament was prepared by dissolving in a liquid agent a solid medicament contained and stored a medical container, a lot of insoluble fine particles were observed. It was confirmed by infrared absorption analysis that the remaining liquid component contained a polyethylene structure. In the case of extracting with n-hexane first, since a liquid component and a solid component remain at the same time after the evaporation to dryness, it becomes difficult to determine only the liquid component. Therefore, it is preferable that the extraction with n-hexane is finally performed in the extractions with the nonpolar organic solvents. It is the most preferable to extract first with acetone, then with n-pentane and finally with n-hexane, that is, in the above mentioned sequence.

As described above, in the present invention, regarding the layer (i) formed of the linear polyolefin, a branching degree of a component, which remains after the Soxhlet's extraction with n-hexane followed by evaporation of n-hexane, is 50 or less per 1,000 carbon atoms (condition (b)). The branching degree is measured by $^1$H-nuclear magnetic resonance spectrum analysis. The branching degree per 1,000 carbon atoms is determined by a proportion of methylene carbons to the entire carbons and a method of measuring the branching degree is well known. The details of such measuring method used in the present invention can be referred to, for example, T. Usami & S. Takayama, Macromolecules, 17, 1756-1761 (1984). The disclosure of this document is incorporated by reference herein.

It was confirmed that the remaining component under the condition (b) is a hydrocarbon having an average molecular weight of about 1,000 or less in the present invention, which contains a linear polyethylene having a low branching degree and has a higher melting point among hydrocarbons having the same molecular weights, and therefore transfer to the surface is suppressed. To the contrary, it is considered that a polyethylene having a higher branching degree is likely to transfer as a liquid component to the surface, and thus causing an interaction with the medicament. The reason why a melting point varies with the branching degree includes an influence of an intermolecular force in the linear polyolefin, and specifically, van der Waals force, interaction between dipoles and/or hydrogen bond is exemplified. For example, only van der Waals force is important in the case of a saturated hydrocarbon. When the branching degree of the hydrocarbon increases, the surface area decreases as compared with a linear hydrocarbon, and thus van der Waals force decreases so that a boiling point and a melting point thereof become lower. As a result of this influence, it is considered that, when a component having a branching degree, particularly a branching degree per 1,000 carbon atoms, of more than 50 is contained, the degree of transferring to the surface as the liquid component increases, and thus causing the interaction with the medicament.

As described above, in the medical container of the present invention, the layer (i) formed of the linear polyolefin constitutes a portion or all of the surface exposed to the inside of the container. According to the demand required to the medicament to be contained, the proportion of the layer (i) formed of the linear polyolefin to the exposed surface can be appropriately selected. As a matter of course, the entire exposed surface is more preferably composed of the layer (i) formed of the linear polyolefin. This layer (i) formed of the linear polyolefin satisfies at least one of the condition (a) and the condition (b), and more preferably both conditions.

The methods for preparation of polyethylene are classified into a high pressure method for synthesis using a radical polymerization initiator and a high pressure of 500 to 7,000 atmospheric pressure, a middle pressure method for synthesis using a metal oxide-based catalyst and a middle pressure of 30 to 40 atmospheric pressure, and a low pressure method for synthesis using a Ziegler catalyst and a low pressure of 10 atmospheric pressure or less.

In the case of the high-pressure low-density polyethylene, branching is formed by the chain transfer reaction during the polymerization using only ethylene as a material, and the number of short-chain branching is adjusted by copolymerization with the other α-olefin, thereby controlling the density. Main factors which affect on physical properties of polyethylene are for example a structure factor such as a molecular weight, a molecular weight distribution, and a structural factors such as a branch number, and kind and distribution of branches, and polyethylene having various properties can be obtained by variation of these factors.

As a new method, there has been developed a method for preparing a linear low-density polyethylene having properties similar to those of the low-density polyethylene wherein ethylene is copolymerized with a comonomer such as butene-1 under a middle or low pressure with low energy consumption.

In the present invention, when the linear polyolefin is a polyethylene, without being restrained by the above described methods for synthesis, the intended object can be achieved by selecting the above described amount of the remaining liquid component after extracting with the above solvents and/or the above described branching degree of the component after extracting with n-hexane.

The cyclic polyolefin used in the present invention may be any known cyclic polyolefin as long as it can be used for the medical container of the present invention, and can include thermoplastic saturated norbornene-based polymers (for example, those disclosed in Japanese Unexamined Patent Publication (Kokai) Nos. 4-276253, 5-317411 and 8-155007) can be used. Specific examples thereof include a polymer having a structural unit represented by the following Chemical Formula 1, a polymer having a structural unit represented by the following Chemical Formula 2, and a polymer having structural units represented by the following Chemical Formula 1 and Chemical Formula 2:

[Chemical Formula 1]

In the above formula, $R_1$ and $R_2$ represent hydrogen or a hydrocarbon residue having 1 to 10 carbon atoms and may be the same or different, and $R_1$ and $R_2$ may be combined with each other to form a ring, and n represents a positive integer, and

[Chemical Formula 2]

In the above formula, $R_3$ and $R_4$ represent hydrogen or a hydrocarbon residue having 1 to 5 carbon atoms and may be the same or different, and $R_3$ and $R_4$ may be combined with each other to form a ring, and l and m each represents a positive integer, and p represents 0 or a positive integer.

The polymer having a structural unit represented by Chemical Formula 1 includes a saturated polymer prepared by using the following as a monomer, polymerizing the monomer in a known ring-opening polymerization method to obtain a ring-opened polymer, and hydrogenating the obtained ring-opened polymer using a conventional hydrogenation method:

2-norbornene, and its alkyl and/or alkylidene substituted compounds such as 5-methyl-2-norbornene, 5,5-dimethyl-2-norbornene, 5-ethyl-2-norbornene, 5-butyl-2-norbornene, and 5-ethylidene-2-norbornene;

dicyclopentadiene, 2,3-dihydrodicyclopentadiene, and alkyl substituted compounds thereof obtained by substitution with methyl, ethyl, propyl and butyl group;

dimethanooctahydronaphthalene, and alkyl and/or alkylidene substituted compounds thereof such as 6-methyl-1,4:5,8-dimethano-1,4,4a,5,6,7,8,8a-otcahydronaphthalene, 6-ethyl-1,4:5,8-dimethano-1,4,4a,5,6,7,8,8a-otcahydronaphthalene, and 6-ethylidene-1,4:5,8-dimethano-1,4,4a,5,6,7,8,8a-otcahydronaphthalene; and trimers to tetramers of cyclopentane such as 4,9:5,8-dimethano-3a,4,4a,5,8,8a,9,9a-octahydro-1H-benzoindene, 5,8-methano-3a,4,4a,5,8,8a,9,9a-octahydro-1H-benzoindene, 5,8-methano-1,4,4a,4b,5,8,8a,9b-octahydro-1H-fluorene, and 4,11:5,10:6,9-trimethano-3a,4,4a,5,5a,6,9,9a,10,10a,11,11a-dodecahydro-1H-cyclopentaanthracene.

Examples of the polymer having a structural unit represented by Chemical Formula 2 include a polymer obtained by copolymerizing the above described norbornene-based monomer and ethylene as monomers and/or its hydrogenated polymer, both of which are saturated polymers.

With respect to the cyclic polyolefin used in the present invention, the thermoplastic saturated norbornene-based polymer may be a hydrogenated substance of a ring-opened polymer of a polar monomer, or a copolymer of the norbornene-based polymer and ethylene, or a hydrogenated substance of such copolymer.

The cyclic polyolefin used in the present invention is preferably a thermoplastic saturated norbornene-based polymer composed only of the above mentioned monomer having no polar group in view of the moisture impermeability, but may be a polymer obtained by partially copolymerizing with a polar monomer as long as the object of the present invention is not impaired.

The cyclic polyolefin may be a blend with other polymer as long as it does not exert an adverse influence on the medical container of the present invention. Examples of such other polymer include a high-density polyethylene, a middle-density polyethylene and a polypropylene-based resin.

Examples of the linear polyolefin layer adjacent to the cyclic polyolefin layer (layer (i) and layer (v)) include layers formed of linear polyolefins such as a low-density polyethylene, a linear low-density polyethylene, a middle-density polyethylene, a high-density polyethylene, a polypropylene and an ethylene/propylene copolymer. It is not necessarily that the layer (v) formed of the linear polyolefin satisfies the condition (a) and/or the condition (b).

The multilayered film constituting the medical container of the present invention comprises (i) the layer formed of the linear polyolefin and (ii) the layer formed of the cyclic polyolefin adjacent to the layer (i) and, furthermore, (v) the layer formed of the linear polyolefin is adjacent to the layer (ii) formed of the cyclic polyolefin, if necessary.

The thickness of the linear polyolefin layer (i) is usually from 10 to 500 μm, and preferably from 20 to 300 μm, and the thickness of the cyclic polyolefin layer (ii) is usually from 10 to 500 μm, and preferably from 20 to 300 μm. Also, the thickness of the linear polyolefin layer (v) is usually from 10 to 500 μm, and preferably from 20 to 300 μm.

It is preferable that the multilayered film constituting the medical container of the present invention further comprises the printable layer and/or the barrier layer on the layer (ii) formed of the cyclic polyolefin or the layer (v) formed of the linear polyolefin. The printable layer is, for example, a polyester layer or a polyester layer having an inorganic substance deposited thin film, and its thickness is usually from 5 to 50 μm. When the barrier layer is, for example, a metal foil or a synthetic resin layer, its thickness is usually from 5 to 50 μm.

In one embodiment of the multilayered film constituting the medical container of the present invention, (i) the layer formed of the linear polyolefin, (ii) the layer formed of the cyclic polyolefin adjacent to the layer (i), (iii) the polyester layer or the polyester layer having an inorganic substance deposited thin film and (v) the linear polyolefin layer are preferably laminated in the above mentioned sequence. The layer (i) formed of the linear polyolefin, the polyester layer or the polyester layer having an inorganic substance deposited thin film (iii) and the linear polyolefin layer (v) are preferably laminated via an adhesive layer. In the present description, the adhesive layer means a layer formed of an adhesive resin or an adhesive, which enables bonding of the layer (ii) containing the cyclic polyolefin and the other layer, or bonding of other two layers.

In other embodiment of the multilayered film constituting the medical container of the present invention, (i) the layer formed of the linear polyolefin, (ii) the layer formed of the cyclic polyolefin adjacent to the layer (i), (v) the layer formed of the linear polyolefin adjacent to the layer (ii), (iii) the polyester layer or the polyester layer having the inorganic substance deposited thin film and (v) the linear polyolefin layer are laminated in the above mentioned sequence. The layer (i) formed of the linear polyolefin, the polyester layer or the polyester layer having the inorganic substance deposited thin film (iii) and the linear polyolefin layer (v) are preferably laminated via the adhesive layer.

As the method for producing the multilayered film used in the medical container of the present invention, any proper laminating method may be used. Examples thereof include a dry lamination method, an extrusion lamination method, a coextrusion lamination method (T-die method, inflation method), a heat lamination, or a lamination method as any combination of these methods. As described above, the layer (i) formed of the linear polyolefin and the layer (ii) formed of the cyclic polyolefin adjacent to the layer (i) are an adjacent state of being in direct contact with each other, and the other layers may be in direct contact, or an adhesive layer may be formed between the layer and the other layer. The above mentioned lamination methods are known and person skilled in the art can select an optimum method according to the kind of the layers to be laminated and the presence or absence of the adhesive layer.

As described above, the adhesive layer is a layer formed of an adhesive or an adhesive resin which is located between the layers in the case of laminating the layers so as to bond these layers. The adhesive includes a polyurethane-based adhesive, and the adhesive resin includes the above mentioned polyolefins, an acid-modified polyolefin modified with an acid such as maleic anhydride, and a copolymer of ethylene and a monomer having a carboxyl group. The thickness of the adhesive layer is appropriately selected according to the kind and thickness of the film to be bonded.

As the method for producing the medical container of the present invention using the multilayered film, for example, there may be used any proper method, for example vacuum forming, sheet forming technique (thermoforming method) such as air-pressure forming, blow molding method such as multilayer coextrusion blow molding, or a method for producing a bag-shaped product by heat-sealing peripheral portions of multilayered films in the sheet forms cut into predetermined shapes, or by bonding such peripheral portions using an adhesive.

In one embodiment, the medical container of the present invention is characterized in that the above mentioned multilayered films are bonded with each other, such that the layers formed of the linear polyolefin are located as the innermost layers and the layers formed of the cyclic polyolefin are located as the intermediate layers.

By constituting the intermediate layer with the layer formed of the cyclic polyolefin, it becomes possible to more decrease amounts of a lower molecular weight component and an adhesive layer component which are eluted from the container. Since the cyclic polyolefin has a higher density than that of the polyethylene and also has a three-dimensional structure, molecular motion of the polymer can be suppressed when compared with the linear polyolefin. The medical container of the present invention has a layer configuration wherein the layer formed of the linear polyolefin as a sealant and a cyclic polyolefin are bonded and it is also possible to suppress an elution component from the linear polyolefin itself since the molecular motion ability of the linear polyolefin is suppressed by the cyclic polyolefin.

Since the linear polyolefin constituting the innermost layer adjacent to the cyclic polyolefin has stable sealability as a sealant and shows its wide selection for a combination with another member which exhibits easy peeling performance, it is suited for the use as the innermost layer of the medical container. Since the linear polyolefin of this innermost layer constitutes the layer with which various medicaments are brought into contact, it is preferable to use the linear polyolefin containing an elusion component in an amount as small as possible. Therefore, a linear polyolefin, which satisfies that the amount of the liquid component, which remains after the Soxhlet's extractions with the organic solvents each followed by the evaporation of the solvent, is 0.2% by weight or less, and/or the branching degree of the component, which remains after the Soxhlet's extraction with n-hexane followed by the evaporation of n-hexane, is 50 or less per 1,000 carbon atoms, is selected. In the container of the present invention, when the multi-layered film comprises the polyester layer, rigidity of the container such as a bag can be improved and it becomes possible to perform printing. In addition, when the multi-layered film comprises the metal foil, the metal deposited layer or the inorganic substance deposited layer, barrier properties against for example ultraviolet ray, steam or gas can be improved. As a result, the medical container of the present invention can store a medicament which is unstable against for example ultraviolet ray, moisture and/or oxygen.

As described above, in the medical duplex container of the present invention, one or more compartments containing the liquid agent and one or more compartments containing the medicament are liquid-tightly partitioned by a peelable weakly fused portions and, when the container is used, the weakly fused portion is peeled off by pressing the container with hands or a jig from its outside, thereby mixing the liquid agent with the medicament to give a formulated medicament.

In one embodiment of the medical duplex container of the present invention, the liquid agent compartment containing the liquid agent and the medicament compartment containing the medicament are liquid-tightly partitioned by the peelable seal portion and the medicament compartment includes a bag-shaped container composed of a front sheet and a rear sheet, while the liquid agent compartment includes a bag-shaped container (or a tube-shaped container) formed from a tube-shaped film. One embodiment of the duplex container comprising one each compartment is shown as a schematic sectional view and a schematic plan view in FIGS. 1 and 2, respectively. In the drawings, the symbol 1 denotes a duplex container, 2 denotes a liquid agent compartment (for example, a liquid medicament compartment), 3 denotes a medicament compartment (for example, a powder medicament compartment), 4 denotes a front sheer, 5 denotes a rear sheet, 6 denotes a peelable seal portion, and 7 denotes a port.

In one embodiment of the medical duplex container of the present invention, the liquid agent compartment containing the liquid agent and the medicament compartment containing the medicament are liquid-tightly partitioned by the peelable seal portion, and the medicament compartment is a bag-shaped container composed of a front sheet and a rear sheet, while the front sheet of the medicament compartment is formed of a multilayered film comprising at least four layers, (i) the layer formed of the linear polyolefin (the innermost layer), (ii) the layer formed of the cyclic polyolefin adjacent to the layer (i) (an intermediate layer), (iii) the polyester layer or the polyester layer having the inorganic substance deposited thin film (an intermediate layer) and (v) the linear polyolefin layer (the outermost layer), which are laminated in the above described sequence.

In other embodiment of the medical duplex container of the present invention, the liquid agent compartment containing the liquid agent and the medicament compartment containing the medicament are liquid-tightly partitioned by the peelable seal portion, and the medicament compartment is a bag-shaped container composed of a front sheet and a rear sheet, while the rear sheet of the medicament compartment is formed of a multilayered film comprising at least four layers, (i) the layer formed of the linear polyolefin (the innermost layer), (ii) the layer formed of the cyclic polyolefin adjacent to the layer (i) (an intermediate layer), (iv) the metal foil, the metal deposited layer or the inorganic substance deposited layer (an intermediate layer) and (iii) the polyester layer (the outermost layer), which are laminated in the above described sequence.

In a specific embodiment of the medical duplex container of the present invention, the liquid agent compartment containing the liquid agent and the medicament compartment containing the medicament are liquid-tightly partitioned by the peelable seal portion, and the medicament compartment is a bag-shaped product composed of a front sheet and a rear sheet, while the front sheet of the medicament compartment is formed of a multilayered film comprising at least four layers, (i) the layer formed of the linear polyolefin (the innermost layer), (ii) the layer formed of the cyclic polyolefin adjacent to the layer (i) (an intermediate layer), (iii) the polyester layer or the polyester layer having the inorganic substance deposited thin film (an intermediate layer) and (v) the linear polyolefin layer (the outermost layer) laminated in the above described sequence, and the rear sheet of the medicament compartment is formed of a multilayered film comprising at least four layers, (i) the layer formed of the linear polyolefin (the innermost layer), (ii) the layer formed of the cyclic polyolefin adjacent to the layer (i) (an intermediate layer), (iv) the metal foil, the metal deposited layer or the inorganic substance deposited layer (an intermediate layer) and (iii) the polyester layer or the polyester layer having the inorganic substance deposited thin film (the outermost layer) which are laminated in the above described sequence.

The front sheet of the above described medicament compartment is formed of a multilayered film in which (i) the layer formed of the linear polyolefin (the innermost layer), (ii) the layer formed of the cyclic polyolefin adjacent to the layer (i) (an intermediate layer), (iii) the polyester layer or the polyester layer having the inorganic substance deposited thin film (an intermediate layer) and (v) the linear polyolefin layer (an outermost layer) are laminated in the above described sequence (see FIG. 3). Also, the rear sheet of the above described medicament compartment is formed of a multilayered film in which (i) the layer formed of the linear polyolefin (the innermost layer), (ii) the layer formed of the cyclic polyolefin (an intermediate layer), (iv) the metal foil, the metal deposited layer or the inorganic substance deposited layer (an intermediate layer) and (iii) the polyester layer (the outermost layer) are laminated in the above described sequence (see FIG. 4).

Furthermore, in other embodiment of the medical duplex container of the present invention, the front sheet of the medicament compartment is formed of a multilayered film comprising at least five layers in which (i) the layer formed of the linear polyolefin (the innermost layer), (ii) the layer formed of the cyclic polyolefin adjacent to the layer (i) (an intermediate layer), (v) the linear polyolefin layer (an intermediate layer), (iii) the polyester layer or the polyester layer having the inorganic substance deposited thin film (an intermediate layer) and (v) the linear polyolefin layer (the outermost layer) are laminated in the above described sequence.

In a specific embodiment of the duplex container of the present invention, the front sheet of the medicament compartment is formed of a multilayered film comprising at least five layers in which (i) the layer formed of the linear polyolefin (the innermost layer), (ii) the layer formed of the cyclic polyolefin adjacent to the layer (i) (an intermediate layer), (v) the linear polyolefin layer (an intermediate layer), (iii) the polyester layer or the polyester layer having the inorganic substance deposited thin film (an intermediate layer) and (v) the linear polyolefin layer (the outermost layer) are laminated in the above described sequence, and the rear sheet of the medicament compartment is formed of a multilayered film comprising at least three layers in which (i) the layer formed of the linear polyolefin (the innermost layer), (v) the metal foil, the metal deposited layer or the inorganic substance deposited layer (an intermediate layer) and (iii) the polyester layer (the outermost layer) are laminated in the above described sequence.

The front sheet of the medicament compartment is composed of a multilayered film in which (i) the layer formed of the linear polyolefin (the innermost layer), (ii) the layer formed of the cyclic polyolefin adjacent to the layer (i) (an intermediate layer), (v) the layer formed of the linear polyolefin adjacent to the layer (ii), (iii) the polyester layer or the polyester layer having an inorganic substance deposited thin film (an intermediate layer) and (v) the linear polyolefin layer (the outermost layer) are laminated in the above described sequence (see FIG. 5). Also, the rear sheet of the medicament compartment is composed of a multilayered film in which (i) the layer formed of the linear polyolefin (the innermost layer), (iv) the metal foil, the metal deposited layer or the inorganic substance deposited layer (an intermediate layer) and (iii) the polyester layer or the polyester layer having the inorganic substance deposited thin film (the outermost layer) are laminated in the above described sequence (see FIG. 6).

The above described liquid agent compartment is composed of a single layer formed of a polyolefin-based resins, or a multilayered film comprising layers formed of a polyolefin-based resin(s), or a multilayered film comprising a layer formed of a polyolefin-based resin and a layer formed of the other resin. Specifically, a bag-shaped container obtained by liquid-tightly bonding (that is, strongly sealing) peripheral portions of such two films, or a tube-shaped container of such film is preferable. Examples of the polyolefin-based resin include a low-density polyethylene, a linear low-density polyethylene, a middle-density polyethylene, a high-density polyethylene, a polypropylene, ethylene-propylene copolymer, or a blend thereof. The thickness of the liquid agent compartment is not specifically limited and is usually selected according to the thickness of the medicament compartment. In other embodiment, the liquid agent compartment may be composed of the multilayered film constituting the above described medicament compartment.

The liquid agent compartment containing a liquid agent and the medicament compartment containing a medicament are liquid-tightly partitioned by a peelable seal portion. The peelable seal portion is a portion having an easily peeling function which is formed by fusing portions of the innermost layers constituting the medicament compartment and/or the liquid agent compartment, or by weakly fusing a portion of other member (for example, sheet-like member) formed of a resin having smaller fusion strength to the innermost layer and the innermost layer. The easily peeling function means a function of the fused portion capable of easily peeling off by a force, which can be applied by hands or a jig (for example, by pressing the medicament compartment by a force with hands) in the case of formulating a medicament by mixing a medicament with a liquid agent after the films constituting the container are sealed by bonding with each other. Examples of the material constituting other member described above include a blend polymer of a polyethylene and a polypropylene, an ethylene/propylene copolymer, and a blend of a propylene/α-olefin copolymer (A) and a propylene-α-olefin copolymer (B) having an α-olefin content different from that of the copolymer (A) and/or a propylene homopolymer (C) (see Japanese Unexamined Patent Publication (Kokai) No. 2001-226499). The container having the above peelable seal portion is known (see, for example, Japanese Patent No. 3,016,348 and Japanese Unexamined Patent Publication (Kokai) No. 2003-104391).

Examples of the liquid agent to be contained in the liquid agent compartment of the medical duplex container of the present invention include water for injection, physiological saline, glucose solution, amino acid solution, high calorie infusion solution, fat emulsion, vitamin preparation, and metal element preparation.

Examples of the medicament to be contained in the medicament compartment of the medical container of the present invention include a solid or liquid medicament, and examples of such medicament include antibiotic agent, antibacterial agent, anticancer agent, hormone agent and Chinese medicine. The container of the present invention is particularly preferable so as to store the antibiotic agent. For example, when a powder solid medicament is contained, close attention must be paid to moisture or gas permeation. The solid medicament means a medicament in a solid state and a powdered medicament is preferable as described above. In other embodiment, the medicament may be in the form of granule or tablet.

By the way, the method for measurement of the number of insoluble fine particles in an injection is described in the section of an injection product of formulation general rules of the Japanese Pharmacopoeia. In principle, "method with light-shielding type automatic fine particle counter" as the first method is used and, if the measurement can not be performed by the first method, the measurement can be performed using "method with microscope" as a second method.

As criteria for the injection product, it is necessary that the number of particles having a particle size of 10 μm or more per 1 mL is 25 or less, and the number of particles having a particle size of 25 μm or more per 1 mL is 3 or less when measured by the first method. Therefore, the medical container, particularly the medical duplex container of the present invention is particularly useful for a medicament which does not meet the above criteria when testing it with the conventional medical duplex container (for example, a medical duplex container described in Comparative Examples of the present description).

As criteria for the injection product, it is necessary that the number of particles having a particle size of 10 μm or more per 1 mL is 12 or less, and the number of particles having a particle size of 25 μm or more per 1 mL is 2 or less when measured by the second method. Therefore, similarly to the above case, the medical container, particularly the medical duplex container of the present invention is particularly useful for a medicament which does not meet the above criteria when testing it with the conventional medical duplex container.

EXAMPLES

The medical container of the present invention will now be described in detail by way of Examples and Comparative Examples. In the Examples and the Comparative Examples, the respective measurement items were measured by the following procedures.

Content of Liquid Component (Relating to the Condition (a))

10 g of a single-layered film formed of a material to be measured (for example, a linear polyethylene) is Soxhlet extracted with methanol (300 ml) for 7 hours to obtain an extract solution, and methanol is removed from the extract solution by evaporation using an evaporator. When the remaining substance is an oily substance, it is weighed. Then, the film after extracting with methanol is extracted with acetone (300 ml) for 7 hours. Similarly, when the remaining substance is an oily substance, it is weighed. The same operations are repeated successively using n-pentane (300 ml) and n-hexane (300 ml) each followed by the Soxhlet's extraction, and then the removal of the solvent from each extract solution using an evaporator. When the description of each residue is observed and the residue is a liquid substance, its weight is measured. The total weight of the liquid substances is calculated and the proportion of the total weight to the weight of the film is determined. Using this proportion as the content of the liquid component, it is judged whether or not the condition (a) is satisfied.

Branching Degree of Branching of Low Molecular Weight Component (Relating to the Condition (b))

10 g of a single-layered film formed of a material to be measured (for example, a linear polyethylene) is Soxhlet extracted with n-hexane for 6 hours to obtain an extract solution, and the solvent is removed from the extract solution by evaporation using an evaporator. The residue was subjected to $^1$H-nuclear magnetic resonance spectrum analysis and a proportion of methylene carbons to the entire carbons is determined as the number of branching per 1,000 carbons. Based on this branching degree, it is judged whether or not the condition (b) is satisfied.

Specifically, $^{13}$C-NMR spectrum was measured by a nuclear magnetic resonance spectrometer (Model EX-270, manufactured by JEOL, Ltd., $^1$H nuclear magnetic resonance frequency: 270 MHz). Using deuterated tetrachloroethane as a solvent for the remaining component and using an NMR sample tube having a diameter of 5 mm, the measurement was conducted at the concentration of the remaining component of 25 mg/0.6 ml at 50° C. Using tetramethylsilane as an internal reference, data were integrated 12,000 times at a pulse of 450 under the conditions of an observation range of 15,000 Hz, a data point of 32,000 and a repeating time of 5 seconds.

Insoluble fine particles in the liquid medicament: Using a light-shielded automatic fine particle counter (KL-01, manufactured by RION Co., Ltd.) or a liquid insoluble fine particle counter (Hiac/Royco 8000A), the number of insoluble fine particles is measured by a test method in accordance with the in-liquid insoluble fine particle test in the Japanese Pharmacopoeia. The principle of the light-shielding automatic fine particle counting is as follows: Insoluble fine particles in a dissolving liquid suctioned at a fixed flow rate are scattered through laser light irradiated. The frequency of this scattered light is converted into a numerical value and the intensity of the scattered light is converted to a diameter of the particle, thereby counting the measured values.

Example 1

Production of Front Sheet

A middle-density polyethylene (density: 0.938 g/cm$^3$, manufactured by Ube Industries, Ltd., trade name: UMERIT, for the inner layer) and a cyclic polyolefin (manufactured by Zeon Corporation, trade name: Zeonoa, for the outer layer) were extruded at 300° C. using a coextruder to obtain a two-layered film (thickness of the inner layer: 30 μm, thickness of the outer layer: 20 μm) On the cyclic polyolefin layer of this two-layered film, a polyethylene terephthalate film (manufactured by Mitsubishi Chemical Corporation, thickness: 12 μm) and a middle-density polyethylene film (density: 0.938 g/cm$^3$, manufactured by Ube Industries, Ltd., trade name: UMERIT, thickness: 40 μm) were laminated in sequence each via a polyolefin-based adhesive resin (LLDPE) to obtain a four-layered film (A1) as a multi-layered film. The thickness of each adhesive resin (LLDPE) was 20 μm. Referring to the number of layers constituting the multi-layered film, the number of the adhesive layer is not included (the same shall be applicable hereinafter).

Production of Rear Sheet

A middle-density polyethylene (density: 0.938 g/cm$^3$, manufactured by Ube Industries, Ltd., trade name: UMERIT, for the inner layer) and a cyclic polyolefin (manufactured by Zeon Corporation, trade name: Zeonoa, for the outer layer) were extruded at 170° C. using a coextruder to obtain a two-layered film (thickness: 40 μm). Separately, an aluminum foil (manufactured by Sun-Aluminium Ind., Ltd., thickness: 20 μm) and a polyethylene terephthalate film (manufactured by Toyobo Co., Ltd., thickness: 16 μm) were laminated using a polyurethane-based adhesive A520/A50 (manufactured by Takeda Pharmaceutical Company Limited) to obtain a two-layered laminate. On the cyclic polyolefin layer of the two-layered laminate, an aluminum foil of the two-layered laminate was laminated via a polyolefin-based adhesive resin (LLDPE) to produce a four-layered film (B1) as a multi-layered film. The adhesive layer (LLDPE) had a thickness of 20 μm.

Production of Bag-Shaped Container

Using a heat sealer, three peripheral sides of each of the above four-layered film (A1) and the above four-layered film (B1) were strongly sealed at 140° C. under pressure of 0.3 MPa so that the middle-density polyethylene layers were is located as the innermost layers to produce a bag-shaped container having a size of 140 mm×115 mm.

Production of Sample

A powder antibiotic agent was contained in the above bag-shaped container, followed by strong sealing to obtain a sample. The sample was stored at 50° C. for 3 months, and the powder antibiotic agent was taken out and dissolved in 100 ml of physiological saline, and then the number of liquid insoluble fine particles was measured by the in-liquid insoluble fine particle counter (KL-04, manufactured by RION Co., Ltd.). The configurations of the layers are shown in Table 1 and the results are shown in Table 2.

Example 2

Production of Front Sheet

A middle-density polyethylene (density: 0.938 g/cm$^3$, manufactured by Ube Industries, Ltd., trade name: UMERIT, for the inner layer), a cyclic polyolefin (manufactured by Zeon Corporation, trade name: Zeonoa, for the intermediate layer) and a middle-density polyethylene (density: 0.938 g/cm$^3$, manufactured by Ube Industries, Ltd., trade name: UMERIT, for the outer layer) were extruded at 300° C. using a coextruder to obtain a three-layered film (thickness of the inner layer: 30 μm, thickness of the intermediate layer: 20 μm, thickness of the outer layer: 20 μm). On the middle-density polyethylene layer (outer layer) of this three-layered film, a biaxially stretched polyethylene terephthalate film (manufactured by Mitsubishi Chemical Corporation, thickness: 12 µm) and a middle-density polyethylene film (density: 0.938 g/cm$^3$, manufactured by Ube Industries, Ltd., trade name: UMERIT, thickness: 40 µm) were laminated in sequence each via a polyolefin-based adhesive resin (LLDPE) to obtain a five-layered film (A2) as a multi-layered film. The thickness of each adhesive resin (LLDPE) was 20 µm.

Production of Rear Sheet

A middle-density polyethylene film (density: 0.938 g/cm$^3$, manufactured by Ube Industries, Ltd., trade name: UMERIT) was extruded at 170° C. using an extruder to obtain an inner layer film (thickness: 40 µm). Separately, an aluminum foil (manufactured by Sun-Aluminium Ind., Ltd., thickness: 20 µm) and a polyethylene terephthalate film (manufactured by Toyobo Co., Ltd., thickness: 16 µm) were laminated using a polyurethane-based adhesive A520/A50 (manufactured by Takeda Pharmaceutical Company Limited) to obtain a two-layered laminate. On the intermediate polyethylene layer as the inner layer film, the aluminum foil of the two-layered laminate was laminated via a polyolefin-based adhesive resin (LLDPE) to produce a three-layered film (B2). The adhesive layer (LLDPE) had a thickness of 20 µm.

Production of Bag-Shaped Container

Using a heat sealer, three peripheral sides of each of the above five-layered film (A2) and the above three-layered film (B2) were strongly sealed at 140° C. under pressure of 0.3 MPa so that the middle-density polyethylene layers were located as the innermost layers to produce a bag-shaped container having a size of 140 mm×115 mm.

Production of Sample and Measurement

A powder antibiotic agent was stored in the above bag-shaped container, followed by strong sealing to obtain a sample. The sample was stored at 50° C. for 3 months, and the powder antibiotic agent was taken out and dissolved in 100 ml of physiological saline, and then the number of liquid insoluble fine particles was measured by the in-liquid insoluble fine particle counter (KL-04, manufactured by RION Co., Ltd.). The configurations of the layers are shown in Table 1 and the results are shown in Table 2.

Comparative Example 1

Production of Front Sheet

A linear low-density polyethylene (density: 0.930 g/cm$^3$, manufactured by Tosoh Corporation, trade name: NIPOLON, for the inner layer), a cyclic polyolefin (manufactured by Zeon Corporation, trade name: Zeonoa, for the intermediate layer) and a linear low-density polyethylene film (density: 0.930 g/cm$^3$, manufactured by Tosoh Corporation, trade name: NIPOLON, for the outer layer) were extruded at 300° C. using a coextruder to obtain a three-layered film (thickness of an inner layer: 30 µm, thickness of an intermediate layer: 20 µm, thickness of an outer layer: 20 µm). On the linear low-density polyethylene film (the outer layer) of this three-layered film, a polyethylene terephthalate film (manufactured by Mitsubishi Chemical Corporation, thickness: 12 µm) and a linear low-density polyethylene film (density: 0.930 g/cm$^3$, manufactured by Tosoh Corporation, trade name: NIPOLON, thickness: 40 µm) were laminated in sequence each via a polyolefin-based adhesive resin (LLDPE) to obtain a five-layered film (A1'). The thickness of each adhesive resin (LLDPE) was 20 µm.

Production of Rear Sheet

A linear low-density polyethylene film (density: 0.930 g/cm$^3$, manufactured by Tosoh Corporation, trade name: NIPOLON) was extruded at 170° C. using an extruder to obtain an inner layer film (thickness: 40 µm). Separately, an aluminum foil (manufactured by Sun-Aluminium Ind., Ltd., thickness: 20 µm) and a polyethylene terephthalate film (manufactured by Toyobo Co., Ltd., thickness: 16 µm) were laminated using a polyurethane-based adhesive A520/A50 (manufactured by Takeda Pharmaceutical Company Limited) to obtain a two-layered laminate. On the linear low-density polyethylene layer as the inner layer film, the aluminum foil of the two-layered laminate was laminated via a polyolefin-based adhesive resin (LLDPE) to produce a three-layered film (B2). The adhesive layer (LLDPE) had a thickness of 20 µm.

Production of Bag-Shaped Container

Using a heat sealer, three peripheral sides of each of the above five-layered film (A1') and the above three-layered film (B1') were strongly sealed at 140° C. under pressure of 0.3 MPa so that the linear low-density polyethylene layers were located as the innermost layers to produce a bag-shaped container having a size of 140 mm×115 mm.

Production of Sample and Measurement

In the same manner as in Example 1, the sample was stored in the bag-shaped container at 50° C. for 3 months, and then the number of liquid insoluble fine particles was measured by the in-liquid insoluble fine particle counter (KL-04, manufactured by RION Co., Ltd.). The configurations of the layers are shown in Table 1 and the results are shown in Table 2.

Comparative Example 2

A linear low-density polyethylene film (density: 0.930 g/cm$^3$, manufactured by Tosoh Corporation, trade name: NIPOLON, thickness: 60 µm), a silica-deposited polyethylene terephthalate film (manufactured by Mitsubishi Chemical Corporation, thickness: 12 µm), a polyethylene terephthalate film (manufactured by Mitsubishi Chemical Corporation, thickness: 12 µm) and a linear low-density polyethylene film (density: 0.930 g/cm$^3$, manufactured by Tosoh Corporation, trade name: NIPOLON, thickness: 40 µm) were laminated in sequence each via a polyolefin-based adhesive resin to obtain a four-layered film (front sheet A2').

On the other hand, a linear low-density polyethylene film (density: 0.930 g/cm$^3$, manufactured by Tosoh Corporation, trade name: NIPOLON, thickness: 40 µm), an aluminum foil (manufactured by Sun-Aluminium Ind., Ltd., thickness: 20 µm) and a polyethylene terephthalate film (manufactured by Toyobo Co., Ltd., thickness: 16 µm) were laminated using a polyurethane-based adhesive A520/A50 (manufactured by Takeda Pharmaceutical Company Limited) to obtain a three-layered film (rear sheet B2').

In the same manner as in Example 1, the sample was stored in the bag-shaped container at 50° C. for 3 months, and then the number of liquid insoluble fine particles was measured by the in-liquid insoluble fine particle counter (KL-04, manufactured by RION Co., Ltd.). The configurations of the layers are shown in Table 1 and the results are shown in Table 2.

Comparative Example 3

An inner layer film (thickness: 60 µm) obtained by extruding a linear low-density polyethylene (density: 0.930 g/cm$^3$, manufactured by Tosoh Corporation, trade name: NIPOLON) at 170° C., a polyethylene terephthalate film (manufactured by Mitsubishi Chemical Corporation, thickness: 12 µm) and a linear low-density polyethylene film (density: 0.930 g/cm$^3$, manufactured by Tosoh Corporation, trade name: NIPOLON, thickness: 40 µm) were laminated in sequence to obtain a multilayered film (A3'). A polyolefin-based adhesive layer (LLDPE) was used between these layers. The thickness of the adhesive resin was 20 μm.

A linear low-density polyethylene film (density: 0.930 g/cm³, manufactured by Tosoh Corporation, trade name: NIPOLON) was extruded at 170° C. using an extruder to form an inner layer film (thickness: 40 μm). Separately, an aluminum foil (manufactured by Sun-Aluminium Ind., Ltd., thickness: 20 μm) and a polyethylene terephthalate film (manufactured by Toyobo Co., Ltd., thickness: 16 μm) were laminated using a polyurethane-based adhesive A520/A50 (manufactured by Takeda Pharmaceutical Company Limited) to obtain a two-layered laminate. On the linear low-density polyethylene layer as the inner layer film, the aluminum foil of the two-layered laminate was laminated via a polyolefin-based adhesive resin (LLDPE) to produce a three-layered film (B3'). The adhesive layer (LLDPE) had a thickness of 20 μm.

Using a heat sealer, three peripheral sides of each of the above three-layered film (A3') and the above three-layered film (B3') were strongly sealed at 140° C. under pressure of 0.3 MPa so that the linear low-density polyethylene layers are located as the innermost layers to produce a bag-shaped container having a size of 140 mm×115 mm.

A powder antibiotic agent was contained in the above bag-shaped container, followed by strong sealing to obtain a sample. The sample was stored at 50° C. for 3 months, and the powder antibiotic agent was taken out and dissolved in 100 ml of physiological saline, and then the number of liquid insoluble fine particles was measured by the in-liquid insoluble fine particle counter (KL-04, manufactured by RION Co., Ltd.). The configurations of the layers are shown in Table 1 and the results are shown in Table 2.

TABLE 1

| Configuration of multilayered film (left side corresponding to inner layer) | |
|---|---|
| Front sheet | Rear sheet |
| Example 1 | MDPE/COP/PET/MDPE | MDPE/COP/Al/PET |
| Example 2 | MDPE/COP/MDPE/PET/MDPE | MDPE/Al/PET |
| Comparative Example 1 | LLDPE/COP/LLDPE/PET/LLDPE | LLDPE/Al/PET |
| Comparative Example 2 | LLDPE/SiPET/PET/LLDPE | LLDPE/Al/PET |
| Comparative Example 3 | LLDPE/PET/LLDPE | LLDPE/Al/PET |

COP denotes a cyclic polyolefin

COP denotes a cyclic polyolefin.

TABLE 2

Number of insoluble fine particles in liquid medicament (Unit: particles/mL)

| Diameter of fine particle | Example 1 | Example 2 | Comparative Example 1 | Comparative Example 2 | Comparative Example 3 |
|---|---|---|---|---|---|
| 2 μm ≦ | 79 | 615 | 1949 | 5166 | 5072 |
| 5 μm ≦ | 6 | 33 | 111 | 506 | 501 |
| 10 μm ≦ | 1.0 | 2.4 | 6.3 | 14.0 | 27.8 |
| 25 μm ≦ | 0.1 | 0.0 | 0.0 | 0.2 | 0.3 |

Example 3

Production of Liquid Agent Compartment

A tube having a size of 100 mm in diameter×150 mm in length was formed of a linear low-density polyethylene (0.923 g/cm³, thickness: 250 μm). A port was attached to and strongly fused to one end of the tube at 145° C. for 3.0 seconds, while a small piece formed of a blend polymer containing polyethylene and polypropylene was inserted into the other end such that a portion of the small piece protrudes from an opening of the end. Then, the portion into which the small piece is inserted was weakly fused from the outside under pressure of 0.3 MPa at a sealing temperature of 150° C. for 3.5 seconds so that portions next to the small piece (that is, the balance portions) were strongly fused to form a liquid agent compartment. The liquid agent compartment was filled with a liquid for dissolving a powder medicament as a liquid medicament through the port and subjected to steam sterilization after closing a tip of the port using a cap.

Production of Medicament Compartment

The medicament compartment produced in Example 1 was preliminarily subjected to γ-ray sterilization in the state of the bag-shaped container (having a size of 140 mm×115 mm) and a powder medicament as a solid preparation was aseptically contained in the bag-shaped container. A small piece formed of a blend polymer containing polyethylene and polypropylene was inserted into the inside position setbacked slightly from an opening peripheral side of the bag-shaped container and then the portion including the small piece was weakly sealed under a pressure of 0.3 MPa at a seal temperature of 170° C. for 2 seconds, so that the unsealed portions remain between the small piece and the opening peripheral side and between the opening peripheral side portions including no small piece so as to form a medicament compartment.

Production of Duplex Container

Figure 1:
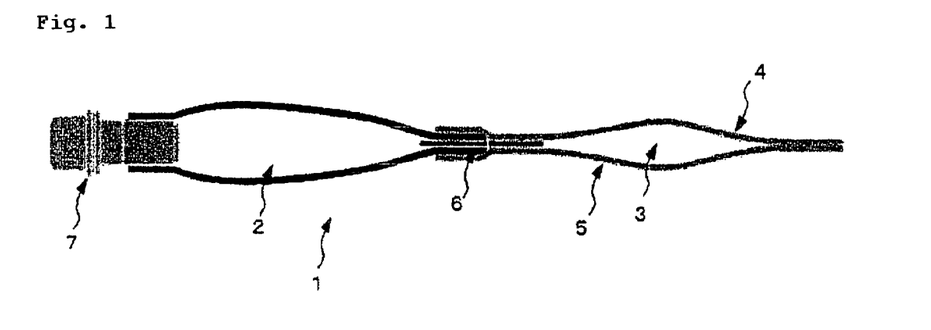
FIG. 1 is a sectional view schematically showing an embodiment of a medical duplex container of the present invention.
Figure 2:
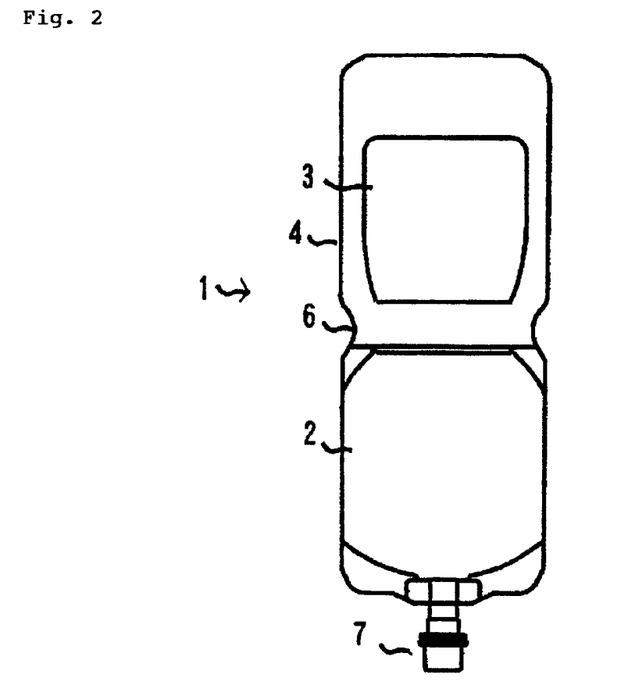
FIG. 2 is a front view schematically showing an embodiment of a medical duplex container of the present invention.

The sealed opening portions of the liquid medicament compartment and the portion of the small piece protruding from the opening were inserted into the unsealed opening peripheral portion near the weakly sealed opening portion of the medicament compartment and the medicament compartment and the liquid medicament compartment were bonded by strongly sealing from the outside under a pressure of 0.3 MPa at a seal temperature of 140° C. for 4.0 seconds to obtain a medical duplex container shown in FIGS. 1 and 2.

Example 4

A middle-density polyethylene (density: 0.938 g/cm³, manufactured by Ube Industries, Ltd., trade name: UMERIT, for the inner layer) and a cyclic polyolefin (manufactured by Zeon Corporation, trade name: Zeonoa, for the outer layer) were extruded using a coextruder to form a two-layered film (thickness of inner layer: thickness: 25 μm, thickness of outer layer: thickness: 30 μm), and then a polyethylene terephthalate film (manufactured by Mitsubishi Chemical Corporation, thickness: 12 μm) and a middle-density polyethylene (density: 0.938 g/cm³, manufactured by Ube Industries, Ltd., trade name: UMERIT, thickness: 40 μm) were laminated in sequence on the cyclic polyolefin as the outer layer each via a polyolefin-based adhesive resin (LLDPE) to form a four-layered film. These films were laminated to each other to obtain a bag-shaped container (having a size of 70 mm×70 mm excluding a seal portion). The film configuration is as follows: MDPE/COP/PET/MDPE (the left side corresponding to the inner layer).

A powder antibiotic agent was contained in the above bag-shaped container, followed by thermal welding to obtain a sample. The sample was stored at 50° C. or 60° C. for a predetermined period and the content medicament was dissolved in 100 mL of physiological saline, and then the number of insoluble fine particles in a dissolving liquid was measured by an in-solution insoluble fine particle counter (Hiac/Royco 8000A). The results are shown in Table 3.

TABLE 3

| | Number of insoluble fine particles in dissolving liquid (Unit: particles/mL) | | |
|---|---|---|---|
| Diameter of fine particle | Before storage | At 50° C. for 3 months | At 60° C. for 2 months |
| 2 μm ≦ | 21.6 | 79.1 | 486.8 |
| 5 μm ≦ | 4.0 | 7.1 | 23.8 |
| 10 μm ≦ | 1.0 | 1.0 | 2.6 |
| 25 μm ≦ | 0 | 0.1 | 0.1 |

Comparative Example 4

With the same layer configuration as in Example 4 except that the portion of the middle-density polyethylene was replaced by a linear low-density polyethylene (density: 0.930 g/cm³, manufactured by Tosoh Corporation, trade name: NIPOLON), a multilayered film was formed. In the same manner as in Example 4, the sample thus obtained was stored under the same conditions and the number of the solution insoluble fine particles was measured similarly. The results are shown in Table 4. The film configuration is as follows: LLDPE/COP/PET/LLDPE (the left side corresponding to the inner layer).

TABLE 4

| | Number of insoluble fine particles in dissolving liquid (Unit: particles/mL) | | |
|---|---|---|---|
| Diameter of fine particle | Before storage | At 50° C. for 3 months | At 60° C. for 2 months |
| 2 μm ≦ | 12.6 | 672.1 | 3051.0 |
| 5 μm ≦ | 2.0 | 24.1 | 106.4 |
| 10 μm ≦ | 0.6 | 0.7 | 1.7 |
| 25 μm ≦ | 0.2 | 0.1 | 0 |

Example 5

Production of Medicament Compartment

A middle-density polyethylene (density: 0.938 g/cm³, manufactured by Ube Industries, Ltd., trade name: UMERIT, for the inner layer), a cyclic polyolefin (manufactured by Zeon Corporation, trade name: Zeonoa, for the intermediate layer) and a middle-density polyethylene (density: 0.938 g/cm³, manufactured by Ube Industries, Ltd., trade name: UMERIT, for the outer layer) were extruded using a coextruder to obtain a three-layered film (thickness of the inner layer: 25 μm, thickness of the intermediate layer: 20 μm, thickness of the outer layer: 15 μm) On the middle-density polyethylene layer as the outer layer, a polyethylene terephthalate film (manufactured by Mitsubishi Chemical Corporation, thickness: 12 μm) and a middle-density polyethylene film (density: 0.938 g/cm³, manufactured by Ube Industries, Ltd., trade name: UMERIT, thickness: 40 μm) were laminated in sequence each via a polyolefin-based adhesive resin (LLDPE) to obtain a five-layered film as a five-layered film (front sheet A5).

Using a middle-density polyethylene (density: 0.938 g/cm³, manufactured by Ube Industries, Ltd., trade name: UMERIT), an inner layer film (thickness: 40 μm) was formed by inflation molding and an aluminum foil (manufactured by Sun-Aluminium Ind., Ltd., thickness: 20 μm) and a polyethylene terephthalate film (manufactured by Toyobo Co., Ltd., thickness: 12 μm) were laminated thereon in sequence each via a polyolefin-based adhesive resin (LLDPE) to form a three-layered film (rear sheet B5).

In the same manner as in Example 3, a rectangular five-layered film (front sheet A5) and a three-layered film (rear sheet B5) were superposed, and a sheet having a weak fusion function formed of a blend of a polyethylene and a polypropylene was interposed between these films slightly inside from one side of the superposed films followed by weak fusion. Further facing edges of the remaining sides of the films were strongly fused so as to form a medicament compartment (a medicament side bag-shaped container having a size of 140 mm in length×115 mm in width). The facing edges between which the sheet was interposed was left as the unfused portions. This medicament compartment was subjected to the γ-ray sterilization in the state of the bag-shaped container, which was aseptically filled with a powder antibiotic agent through an opening of the unfused edge, and then the unfused portion was strongly fused to complete a bag-shaped container.

Production of Liquid Agent Compartment

A tube having a size of 100 m in diameter×150 nm in length was formed of a linear low-density polyethylene (0.923 g/cm³, thickness: 250 μm) and a port was attached to one end of the tube and strongly fused at 145° C. for 3.0 seconds, while a sheet having a weak fusion function formed of a blend of a polyethylene and a polypropylene was inserted at the other end and weakly fused to form a liquid medicament compartment. The liquid agent compartment was filled with 100 ml of a biological saline as a dissolving liquid through the port and subjected to the steam sterilization.

Production of Duplex Container

In the same manner as in Example 3, edges between which the sheet of the liquid medicament was interposed were inserted between edges between which the sheet of the medicament compartment was interposed (that is, between the films A5 and B5 constituting the medicament compartment), followed by strong fusion so as to form a medical duplex container (see FIG. 1). Onto the front sheet side of the medicament compartment, a polypropylene side of a three-layered film obtained by laminating a polyethylene terephthalate film (manufactured by Toyobo Co., Ltd., thickness: 16 μm), an aluminum foil (manufactured by Sun-Aluminium Ind., Ltd., thickness: 20 μm) and a polypropylene film (manufactured by Toray Industries, Inc., trade name: TORAYFAN, thickness: 40 μm) was weakly fused so as to produce a medical duplex container.

Production of Sample and Measurement

This medical duplex container was stored under the conditions of 40° C. and 75% RH, 50° C. or 60° C. for a predetermined period, and then the liquid medicament compartment as a bag for a dissolving liquid was pressed so as to communicate the compartments, thereby dissolving the medicament in the medicament compartment. Then, the number of insoluble fine particles in the dissolving liquid was measured using the in-solution insoluble fine particle counter (Hiac/Royco 8000A). The configurations of the layers are shown in Table 5 and the results are shown in Table 6.

Comparative Example 5

With the same layer configuration as in Example 5, except that the portion of the middle-density polyethylene was replaced by a linear low-density polyethylene (density: 0.930 g/cm$^3$, manufactured by Tosoh Corporation, trade name: NIPOLON), a five-layered film (front sheet A5') was formed.

Using a linear low-density polyethylene (density: 0.930 g/cm$^3$, manufactured by Tosoh Corporation, trade name: NIPOLON), an inner layer film was formed by inflation molding and an aluminum foil (manufactured by Sun-Aluminium Ind., Ltd., thickness: 20 μm) was laminated thereon via a polyolefin-based adhesive and furthermore a polyethylene terephthalate film (manufactured by Toyobo Co., Ltd., thickness: 12 μm) was laminated via a polyurethane-based adhesive resin to form a three-layered film (rear sheet B5').

Using this front sheet A5' and the rear sheet B5', a medicament compartment was produced in the same manner and then combined with a liquid agent compartment to produce a medical duplex container covered with a cover sheet as in Example 5.

This medical duplex container was stored under the conditions of 40° C. and 75% RH, 50° C. or 60° C. for a predetermined period, and then the liquid medicament compartment as a bag for a dissolving liquid was pressed so as to communicate the compartments, thereby dissolving the medicament in the medicament compartment. Then, the number of insoluble fine particles was measured using the in-solution insoluble fine particle counter (Hiac/Royco 8000A). The configurations of the layers are shown in Table 5 and the results are shown in Table 7.

Comparative Example 6

Using a low-density polyethylene (manufactured by Mitsui Chemicals, Inc.), an inner layer film (thickness: 60 μm) was formed by inflation molding, and a silica-deposited polyethylene terephthalate film (manufactured by Mitsubishi Chemical Corporation, thickness: 12 μm), a polyethylene terephthalate film (manufactured by Mitsubishi Chemical Corporation, thickness: 12 μm) and a linear low-density polyethylene film (manufactured by Heisei Polymer Co., Ltd., thickness: 40 μm) were laminated on the inner layer film each via a polyurethane-based adhesive resin to obtain a four-layered film (front sheet A6').

Then, using a low-density polyethylene (manufactured by Mitsui Chemicals, Inc.), an inner layer film (thickness: 40 μm) was formed by inflation molding, and an aluminum foil (manufactured by Sun-Aluminium Ind., Ltd., thickness: 20 μm) and a polyethylene terephthalate film (manufactured by Toyobo Co., Ltd., thickness: 16 μm) were laminated on the inner layer film each via a polyurethane-based adhesive to obtain a three-layered film (rear sheet B6').

Using the above front sheet and the above rear sheet, a medicament compartment was produced and then combined with a liquid agent compartment to produce a medical duplex container covered with a cover sheet in the same manner as in Example 5.

This medical duplex container was stored under the conditions of 40° C. and 75% RH (relative humidity) or 50° C. for a predetermined period and the bag-shape container of the dissolving liquid side was pressed, thereby dissolving the contained medicament while the compartments being communicated. Then, the number of insoluble fine particles in the dissolving liquid was measured using the in-solution insoluble fine particle counter (Hiac/Royco 8000A). The configurations of the layers are shown in Table 5 and the results are shown in Table 8.

TABLE 5

Configuration of multilayered film (left side corresponding to inner layer)

|  | Front sheet | Rear sheet |
|---|---|---|
| Example 5 | MDPE/COP/MDPE/PET/MDPE | MDPE/Al/PET |
| Comparative Example 5 | LLDPE/COP/LLDPE/PET/LLDPE | LLDPE/Al/PET |
| Comparative Example 6 | LDPE/Si-PET/PET/LLDPE | LDPE/Al/PET |

TABLE 6

Number of insoluble fine particles in dissolving liquid (Unit: particles/mL)

| Diameter of fine particles | Before storage | At 40° C. and 75% RH for 6 months | At 50° C. for 3 months | At 60° C. for 2 months |
|---|---|---|---|---|
| 2 μm ≦ | 44.4 | 373.2 | 771.0 | 2309.5 |
| 5 μm ≦ | 4.3 | 21.6 | 68.7 | 203.9 |
| 10 μm ≦ | 0.5 | 1.3 | 5.4 | 12.3 |
| 25 μm ≦ | 0 | 0 | 0.1 | 0.1 |

TABLE 7

Number of insoluble fine particles in dissolving liquid (Unit: particles/mL)

| Diameter of fine particle | Before storage | At 40° C. and 75% RH for 6 months | At 50° C. for 3 months | At 60° C. for 2 months |
|---|---|---|---|---|
| 2 μm ≦ | 26.6 | 630.5 | 3344.8 | 4560 |
| 5 μm ≦ | 2.9 | 64.1 | 204.1 | 267.3 |
| 10 μm ≦ | 0.5 | 1.6 | 4.0 | 10 |
| 25 μm ≦ | 2 | 0 | 0.2 | 0 |

TABLE 8

Number of insoluble fine particles in dissolving liquid (Unit: particles/mL)

| Diameter of fine particle | Before storage | At 40° C. and 75% RH for 6 months | At 50° C. for 3 months |
|---|---|---|---|
| 2 μm ≦ | 17.7 | 3726.3 | 5482.5 |
| 5 μm ≦ | 2.8 | 393.1 | 615.5 |
| 10 μm ≦ | 1.6 | 25.3 | 49.6 |
| 25 μm ≦ | 0.5 | 0.4 | 0.5 |

Reference Example 1

Using a middle-density polyethylene (density: 0.938 g/cm$^3$, manufactured by Ube Industries, Ltd., trade name: UMERIT, MDPE), a linear low-density polyethylene (density: 0.930 g/cm$^3$, manufactured by Tosoh Corporation, trade name: NIPOLON, LLDPE) and a low-density polyethylene (density: 0.920 g/cm$^3$, manufactured by Mitsui Chemicals, Inc., trade name: MIRASON, LDPE), a single-layered film of each polyethylene layer having a thickness of 50 μm was obtained by inflation molding. The content of the liquid components of this film were measured by the method explained in the above. The results are shown in Table 9.

TABLE 9

Content of liquid component after successive solvent extraction (% by weight)

| | Results of successive extraction method | | | | Total content of liquid components |
|---|---|---|---|---|---|
| | Methanol | Acetone | n-pentane | n-hexane | |
| MDPE | 0.07% Liquid | 0.06% Liquid | 0.05% Solid | 0.41% Solid | 0.13% |
| LLDPE | 0.03% Liquid | 0.19% Liquid | 0.09% Liquid | 0.08% Solid | 0.31% |
| LDPE | 0.12% Liquid | 0.22% Liquid | 0.27% Liquid | 1.05% Solid | 0.61% |

Reference Example 2

Using a middle-density polyethylene (density: 0.938 g/cm$^3$, manufactured by Ube Industries, Ltd., trade name: UMERIT, MDPE) and a linear low-density polyethylene (density: 0.930 g/cm$^3$, manufactured by Tosoh Corporation, trade name: NIPOLON, LLDPE), a single-layered film each polyethylene layer having a thickness of 60 μm was obtained by inflation molding. The branching degree of the low molecular weight component of this film was measured by the method explained in the above. The results are shown in Table 10.

TABLE 10

| | Branching degree/1,000 carbon atom of component extracted with n-hexane |
|---|---|
| MDPE | 0 |
| LLDPE | 143 |

The invention claimed is:

1. A medical container comprising a body for containing a medicament characterized in that
the body is formed of a multilayered film which comprises (i) a layer formed of a linear polyolefin wherein the linear polyolefin layer does not contain a cyclic polyolefin, and (ii) a layer formed of a cyclic polyolefin adjacent to said layer (i),
wherein the layer (i) is an innermost layer of the multilayered film, and
the layer (i) formed of the linear polyolefin satisfies the following condition (a) and/or (b):
condition (a): an amount of a liquid component extractable from the layer (i) by Soxhlet extraction with organic solvents followed by evaporation removal of the extraction solvents, is 0.2% by weight or less;
condition (b): a branching degree of a component obtained after extraction from the layer (i) by Soxhlet extraction with n-hexane followed by evaporation removal of the n-hexane, is 50 or less per 1000 carbon atoms.

2. The medical container according to claim 1 wherein said multilayered film comprises (i) the layer formed of the linear polyolefin which does not contain a cyclic polyolefin, (ii) the layer formed of the cyclic polyolefin adjacent to said layer (i), and a printable layer and/or a barrier layer via or not via (v) a layer formed of a linear polyolefin adjacent to the said layer (ii).

3. The medical container according to claim 2 wherein said printable layer is a polyester layer or a polyester layer having an inorganic substance deposited thin film.

4. The medical container according to claim 2 wherein said barrier layer is a metal foil, a metal deposited layer or an inorganic substance deposited layer.

5. The medical container according to claim 1 wherein said multilayered film comprises (i) the layer formed of the linear polyolefin which does not contain a cyclic polyolefin, (ii) the layer formed of the cyclic polyolefin adjacent to said layer (i), (iii) a polyester layer or an inorganic substance deposited polyester layer and (v) a layer formed of a linear polyolefin, which are laminated in the above recited sequence.

6. The medical container according to claim 1 wherein said multilayered film comprises (i) the layer formed of the linear polyolefin which does not contain a cyclic polyolefin, (ii) the layer formed of the cyclic polyolefin adjacent to said layer (i), (iv) a metal foil, a metal deposited layer or an inorganic substance deposited layer and (iii) a polyester layer or an inorganic substance deposited polyester layer, which are laminated in the above recited sequence.

7. The medical container according to claim 1 wherein said multilayered film comprises (i) the layer formed of the linear polyolefin which does not contain a cyclic polyolefin, (ii) the layer formed of the cyclic polyolefin adjacent to said layer (i), (v) a layer formed of
a linear polyolefin adjacent to the said layer (ii), (iii) a polyester layer or an inorganic substance deposited polyester layer and (v) a layer formed of a linear polyolefin, which are laminated in the above recited sequence.

8. The medical container according to claim 1 wherein said body further comprises a port.

9. The medical container according to claim 1 wherein said body constitutes a liquid agent compartment which contains a liquid agent and a medicament compartment liquid-tightly connected with the liquid agent compartment via a peelable seal portion,
said body is a bag-shaped container composed of a front sheet and a rear sheet,
at least one of the liquid agent compartment and the medicament compartment comprises a port, and
the front sheet is formed of said multilayered film.

10. The medical container according to claim 9 wherein said rear sheet is formed of the multilayered film which comprises (i) the layer formed of the linear polyolefin which does not contain a cyclic polyolefin, (ii) the layer formed of the cyclic polyolefin adjacent to said layer (i), (iv) a metal foil, a metal deposited layer or an inorganic substance deposited layer and (iii) a polyester layer or an inorganic substance deposited polyester layer, which are laminated in the above recited sequence.

11. The medical container according to claim 9 wherein said rear sheet is formed of the multilayered film which comprises (i) the layer formed of the linear polyolefin that does not contain a cyclic polyolefin, (iv) a metal foil, a metal deposited layer or an inorganic substance deposited layer and (iii) a polyester layer or an inorganic substance deposited polyester layer, which are laminated in the above recited sequence.

12. The medical container according to claim 9 wherein said liquid agent compartment is made of a single layer film formed of a linear polyolefin or a multilayered film comprising a linear polyolefin.

13. The medical container according to claim 9 wherein said peelable seal portion is a portion formed by weakly fusing the innermost layers of the front sheet and the rear sheet to each other, or a portion formed by weakly fusing said innermost layers with a separate member made of a resin which shows a weak fusion strength with said innermost layers.

14. The medical container according to claim 1 wherein a solid medicament is contained as the medicament.

15. The medical container according to claim 1 which contains, as the medicament, a medicament selected from the group consisting of an antibiotic agent, an antibacterial agent, an anticancer agent and a hormone agent.

16. The medical container according to claim 9 which contains, as the liquid agent,
water for an injection product, a physiological saline, a glucose solution, an amino acid solution, a high calorie infusion solution, a fat emulsion, a vitamin preparation, or
a metal element preparation.

17. The medical container according to claim 1 wherein (i) said linear polyolefin which does not contain a cyclic polyolefin has a density in the range between 0.932 g/cm$^3$ and 0.965 g/cm$^3$.

18. The medical container of claim 1 wherein in the linear polyolefin layer (i) the linear polyolefin is selected from the group consisting of a homopolymer of ethylene, a homopolymer of propylene, and a copolymer of ethylene and an α-olefin.

* * * * *